(12) United States Patent
Boström

(10) Patent No.: US 7,571,645 B2
(45) Date of Patent: Aug. 11, 2009

(54) FLUID LEVEL MEASUREMENT DEVICE

(75) Inventor: Jan Boström, Göteborg (SE)

(73) Assignee: Axsensor AB, Gothenburg (SE)

( * ) Notice: Subject to any disclaimer, the term of this patent is extended or adjusted under 35 U.S.C. 154(b) by 84 days.

(21) Appl. No.: 10/575,896

(22) PCT Filed: Oct. 15, 2004

(86) PCT No.: PCT/SE2004/001483

§ 371 (c)(1),
(2), (4) Date: Dec. 27, 2006

(87) PCT Pub. No.: WO2005/038415

PCT Pub. Date: Apr. 28, 2005

(65) Prior Publication Data

US 2007/0204689 A1   Sep. 6, 2007

(30) Foreign Application Priority Data

Oct. 15, 2003 (SE) .................................. 0302709
Oct. 15, 2003 (SE) .................................. 0302710

(51) Int. Cl.
*G01F 23/28* (2006.01)
(52) U.S. Cl. ................................................. 73/290 V
(58) Field of Classification Search ............... 73/290 R, 73/290 V, 290 B, 640; 367/99, 105; 181/123, 181/124, 125
See application file for complete search history.

(56) References Cited

U.S. PATENT DOCUMENTS

| | | | | |
|---|---|---|---|---|
| 4,909,080 A | * | 3/1990 | Kikuta et al. ............... | 73/290 V |
| 5,062,295 A | * | 11/1991 | Shakkottai et al. ........ | 73/290 V |
| 5,319,973 A | * | 6/1994 | Crayton et al. ............. | 73/290 V |
| 5,471,872 A | * | 12/1995 | Cummings ................. | 73/290 V |
| 6,324,911 B1 | * | 12/2001 | Scarffe ........................ | 73/627 |
| 6,360,599 B1 | * | 3/2002 | Pathak et al. .............. | 73/290 V |
| 7,213,456 B2 | * | 5/2007 | Rollwage et al. .......... | 73/290 V |
| 2004/0182149 A1 | * | 9/2004 | Balin et al. ................ | 73/290 V |

FOREIGN PATENT DOCUMENTS

| | | |
|---|---|---|
| GB | 2164151 | 3/1986 |
| WO | WO 91/19171 | 12/1991 |

OTHER PUBLICATIONS

International Search Report (PCT/ISA/210).

* cited by examiner

*Primary Examiner*—Hezron Williams
*Assistant Examiner*—Gunnar J Gissel
(74) *Attorney, Agent, or Firm*—Harness, Dickey & Pierce PLC

(57) ABSTRACT

The present invention relates to a device (10) for providing a gas composition compensated acoustic measurement of the level of a liquid (16) in a tank (18). The device comprises a transducer (14) arranged outside said liquid for transmitting and receiving acoustic signals, and a waveguide (12) connected to said transducer and extending into the liquid. The device further comprises means for feeding a flow of fluid from said tank into the part of said waveguide which is located above the liquid level. That results in that the gas composition become essentially similar throughout the whole of the waveguide located above the liquid level, whereby the level measurement using the speed of sound in the waveguide, which speed is dependant on gas composition, becomes very accurate.

19 Claims, 6 Drawing Sheets

FLUID LEVEL MEASUREMENT DEVICE

TECHNICAL FIELD

The present invention relates to an improved device for providing an acoustic measurement of the level of a fluid in a tank, which device comprises a transducer arranged outside said liquid for transmitting and receiving acoustic signals, and a waveguide connected to said transducer and extending into the liquid. The present invention also relates to a method for acoustically measuring the liquid level in a tank.

BACKGROUND ART

Measurement devices and methods using acoustic signals are well known in the prior art. Acoustic measurement may for example be used to measure distance, depth, volume, flow rate, or acoustic properties of measurement objects such as attenuation and the like. Often the travel time for an acoustic pulse through a medium, or the travel time for an acoustic pulse back and forth from a reflecting measurement object, is used as a basis for calculation of for example the distance to the measurement object. The distance is basically calculated from the very well known formula distance=velocity*time.

However, the velocity of sound is dependant on for example temperature, which may render the measurement erroneous. To overcome this problem, many acoustic measurement systems comprise a reference system, wherein the acoustic pulse travels a known distance in order to determine the current speed of sound, whereby the current speed of sound then is used to calculate the unknown distance or volume etcetera of the measurement object. A reference system is disclosed in for example UK patent application GB2 164 151.

However, the velocity of sound is also dependent on the composition of the gas which the signal travels through. Often the gas composition varies throughout the measurement device, whereby the speed of sound is different at different parts of the measurement device, which may significantly affect the accuracy of the measurement.

SUMMARY OF THE INVENTION

An object of the present invention is to provide an acoustic measurement device which is improved compared with known acoustic measurement devices.

A particular object is to provide an acoustic measurement device where the measurement is compensated with respect to gas composition.

These and other objects which will become apparent in the following description have now been achieved by an acoustic measurement device of the kind mentioned by way of introduction, further comprising means for feeding a fluid from the tank into the part of the waveguide which is located above the liquid level.

The present invention is based on the understanding that by feeding fluid from the tank through the waveguide it is possible to obtain an atmosphere in the waveguide which is essentially equal throughout the whole of the waveguide above the liquid level. This results that the speed of sound, which depends on gas composition, in the waveguide is compensated with regard to gas composition. Consequently, when using the gas composition compensated speed of sound calculated in relation to a part of the waveguide located above the liquid level in order to determine the liquid level in the tank, this overall level measurement becomes very accurate.

Another advantage with feeding fluid from the tank into the waveguide is that the temperature in the waveguide may become similar throughout the whole of the waveguide above the fluid level. Thus, the speed of sound in the waveguide is additionally compensated with respect to temperature, which also enhances the overall measurement of the liquid level.

In one embodiment of the invention, fluid from the tank is fed into a reference part of the waveguide. The reference part is defined as the part of the waveguide between the transducer and a reference element. The reference element may be for example a protrusion disposed within the waveguide. Fluid that is fed into the reference part may then flow through all of the waveguide positioned above the liquid surface. The fluid flow results in that the gas composition throughout the reference part and the rest of the waveguide is constant, whereby, all else equal, the speed of sound also is constant. This enables a very accurate measurement of the liquid level in the tank.

Preferably, the fluid flow which is fed through the waveguide of the measurement device is small enough for allowing an acoustic signal, for example an acoustic pulse, to travel in said waveguide. Thus, the acoustic pulses that propagates through the waveguide is not significantly affected by the flowing fluid, while at the same time steam may be released from the fluid to create a similar gas composition throughout the waveguide, which as discussed above results in a very accurate measurement.

In another embodiment of the invention, the fluid which is to be fed from the tank into the waveguide is a liquid. An advantage with using a liquid is that the liquid from the tank with ease may be fed into the waveguide. Alternatively, the fluid which is to be fed from the tank into the waveguide is a gas, which for example may be taken from the atmosphere above the liquid surface in the tank.

In a further embodiment, the measurement device is arranged in a tank that further comprises a fuel pump, such as the fuel tank in a car, whereby the flow of fluid in the waveguide is fed by the fuel pump. For example a portion of the fuel reflux originating from the fuel pump may be led into the waveguide. This enables a steady flow of fuel through the waveguide, which as described above results in an accurate measurement. Another advantage with the use of the fuel pump is that no extra feeding device is necessary, which facilitates the construction of the measurement device.

According to a second aspect of the invention the reference part of the measurement device of the kind mentioned by way of introduction further comprises a plurality of drainage holes. One advantage with the drainage holes is that it is possible to get rid of excessive fluid that unintentionally enters the reference part of the measurement device, for example if the tank containing the liquid which is to be measured tilts. Another advantage with the drainage holes is that excess fluid originating from the fluid flow fed to the waveguide may be drawn off. Also, excessive fluid which is a result of condensation in the waveguide may equally be drawn off via the drainage holes.

Note that this aspect of the invention with drainage holes need not be restricted to any particular type of measurement device, but is applicable to any measurement device comprising a waveguide having a part above the fluid surface.

In one embodiment of this second aspect of the invention, the measurement device further comprises an absorbing structure arranged adjacent to said drainage holes. The absorbing structure may for example be an absorbing cloth. By using an absorbing structure in association with the drainage holes, it is possible to reduce disturbances of the acoustic pulses in the waveguide that otherwise may be caused by the drainage holes, and thus obtain a more robust measurement.

The absorbing structure may comprise a main part and at least one end part, whereby the end part is positioned below the main part. This enables that fluid absorbed by the absorbing structure is accumulated in said end because of the siphon effect. The accumulated fluid may then drip off the end of the absorbing structure, for example back into the tank.

In another embodiment of the invention, a part of the waveguide which is located above the liquid level, for example the reference part, is positioned outside of the tank. Further, the measurement device comprises a funnel structure, which has at its bottom end an opening which is in connection with the tank. The funnel structure is so arranged that the waveguide of the measurement object passes through the opening into the tank. During operation, the funnel structure collects fluid that emanates from the drainage holes of the waveguide, and leads the fluid back to the tank through the passage at the bottom of the funnel structure.

The funnel structure may be designed so that the angle of the inner wall of the funnel structure seen from a horizontal plane is larger than a chosen allowed maximum tilt angle of the tank. This means that as long as the tank lends less than the maximum allowed tank tilt angle, the side walls of the funnel structure has such inclination that fluid from the reference part will flow down along the inner side walls and be transferred back to the tank. Consequently, the measurement device will work properly even if the tank tilts (up to a certain limit), which enhances the reliability of the measurement device. Preferable the maximum allowed tank tilt angle is in the range 10-35°.

BRIEF DESCRIPTION OF THE DRAWINGS

Currently preferred embodiments of the invention will now be further described in reference to the accompanying drawings wherein.

DETAILED DESCRIPTION OF PREFERRED EMBODIMENTS

Figure 1:
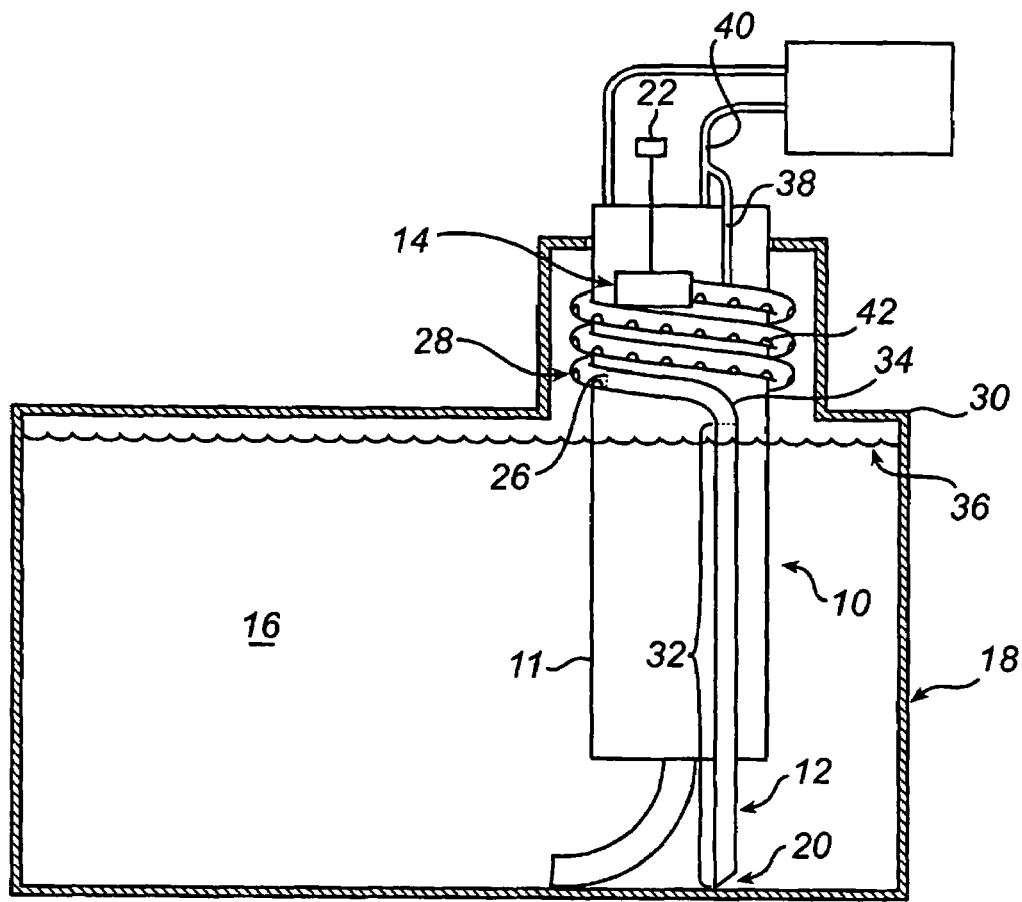
FIG. 1 is a schematic side view of an embodiment of the invention including means for feeding a flow of fluid into the waveguide.

FIG. 1 shows a preferred embodiment of a measurement device according to the present invention. The measurement device is arranged to determine the level of liquid in a tank. The tank may for example be a fuel tank of a boat or a vehicle, such as a car or a truck. The liquid which is to be measured may for example be water, petrol or diesel or the like. The tank shown in FIG. 1 also contains a fuel pump 11.

In FIG. 1, the measurement device 10 according to the invention comprises a waveguide 12 having one end which is connected to a transducer 14, while the other end extends into the fluid 16 which is contained in the tank 18. The end 20 of the waveguide 12 extending into the fluid 16 has an opening to allow fluid to enter the waveguide. Also, the end 20 of the waveguide extending into the fluid is preferably partially fixed to the bottom part of the tank 18. This ensures the position of the end 20 of the waveguide 12, and enables liquid level measurement from the very bottom of the tank.

The abovementioned transducer 14 may for example be a low-cost piezoelectric component, or comprise of a separate sound transmitter and receiver. The transducer is arranged in connection with an electronic control device 22, which is arranged to control the transducer and to compute the liquid level based on the signals transmitted and received by the transducer.

Further, the waveguide 12 comprises a reference element 26, for example a protrusion disposed within the waveguide. The reference element 26 may for example be annularly shaped, or comprise a pin arranged in the wall of the waveguide. The part of the waveguide 12 extending from the end connected with the transducer 14 to the reference element 26 is hereinafter referred to as the reference part 28 of the waveguide. The part of the waveguide 12 from the bottom of the tank 20 to the maximum tank height 30, i.e. the highest possible fluid level, is hereinafter referred to as the measurement part 32 of the waveguide 12. The part of the waveguide 12 between the reference and measurement part is referred to as the "dead" part 34.

The reference part in FIG. 1 have a helical shape, however the reference part may have other shapes, such as a flat spiral shape, or a more elongated shape.

When measuring the liquid level, the transducer 14 is fed with an electric signal from the control device 22 in order to produce an sound pulse. The sound pulse is transmitted from the transducer 14 and guided through the waveguide 12 towards the liquid surface 36. The sound pulse is partially reflected by the reference element 26 at the end of the reference part 28 of the waveguide. The remainder of the pulse passes the dead part 34 and travels through the measurement part 32 until it is reflected by the surface 36 of the liquid. Thus, two reflected pulses return to the transducer 14. One reflected pulse is associated with the reference element, and the other reflected pulse is associated with the surface of the liquid. As a response to the received sound pulses, the transducer 14 generates corresponding electric signals and feeds it back to the control device 22.

The dead part 34 of the waveguide 12 is long enough to ensure that the two pulses reflected from reference element 26 and the fluid surface 36 respectively are sufficiently separated so that the two pulses are distinguishable, even if the tank is filled to the top and thus the pulses are returning to the transducer 14 in relatively close proximity.

By knowing the time interval between each pulse, i.e. the transit time for each acoustic pulse, and the length of the reference part 28, the dead part 34 and the measurement part 32, it is possible for the control device 22 to calculate the liquid level or liquid volume in the tank according to the following formula:

$$\text{Level} = (\text{Reference part} + \text{Dead part} + \text{Measurement part}) - (\text{Reference part}/\text{REF}) * \text{SURF}$$

wherein "reference part", "dead part" and "measurement part" refers to the length of each item respectively, and REF and SURF refers to the transit time for the pulse reflected by the reference element and the liquid surface respectively.

Thus, the liquid level is calculated by reducing the total length of the waveguide with the length of the waveguide above the surface, whereby the length of the waveguide above the surface is calculated as the speed of sound (=Reference part/REF) times the time SURF.

The above calculations are made by the control device 22.

The measurement device further comprises a connection 38 between the reference part 28 of the waveguide and the fuel reflux 40 originating from the fuel pump 11. The connection 38 is a tube which can lead fluid such as petrol. Also, the reference part 28 comprises a plurality of drainage holes 42. Preferably, the reference part 28 contains about 8 drainage holes per round of the helical spiral.

Concurrent with the sound pulses travelling through the waveguide 12 as described above, fluid, in this case fuel, is pumped from the tank by means of the fuel pump 11, through the connection tube 38, and into the reference part 28. Thus, a flow of fuel is continuously pumped through the waveguide 12 during the measurement process. The fuel that travels through the waveguide 12 is returned to the tank 18 through the drainage holes 42 and through the waveguide 12 itself.

On one hand, the extent of the continuous flow through the waveguide 12 is large enough that gas may emanate from the fuel flow, whereby the composition of the gas in the measurement device becomes essentially identical throughout the waveguide. On the other hand, the extent of the flow is small enough that the sound pulses in the reference part 28 are not significantly affected by the fluid itself.

Because of the inventive concurrent flow of fluid through the waveguide and the reference part, the composition of the gas in the reference part 28 is essentially similar throughout the whole of the waveguide located above the liquid level. That means that the speed of sound, which varies depending on gas composition, in the waveguide is compensated with respect to gas composition.

Since the above formula uses the speed of sound according to the reference measurement in order to calculate the liquid level in the tank 18, a very accurate gas composition compensated measurement of the liquid level is obtained.

In the above embodiment, the measurement part 32 is essentially vertical and an absolute measurement of the liquid level is obtained. However, it is also possible to tilt the measurement part in order to make it fit into different tanks with different heights. In that case it is advantageous to calculate the relationship between the liquid level and the maximum level of the tank in order to avoid further calibration, whereby:

Relationship=level/measurement part

In the embodiment of the invention shown in FIG. 1, plane wave propagation is utilized. In order to achieve the plane wave propagation, the wavelength is much larger than the diameter of the waveguide. The wavelength should be longer than approximately the double diameter. The wavelength of the acoustic pulses is preferably in the interval about 2-10 cm, which corresponds to a frequency of about 3,4-17 kHz, i.e. not ultrasound. Because of the relatively long wavelength, the waveguide also has to be long. Preferably, the length of the reference part is up to about 70 cm, and the length of the dead part is up to about 30 cm.

The waveguide 12 in FIG. 1 may also comprise additional reference elements positioned at known distances from the first reference element 26. When using for example one additional reference element, one further sound pulse returns to the transceiver, whereby the transit time of the pulse is used to calculate the current speed of sound. Additional reference elements may for example be positioned in the measurement part, or between the transducer and the first reference element. The former results in that the reference part is closer to the liquid when the liquid level is low.

Figure 2:
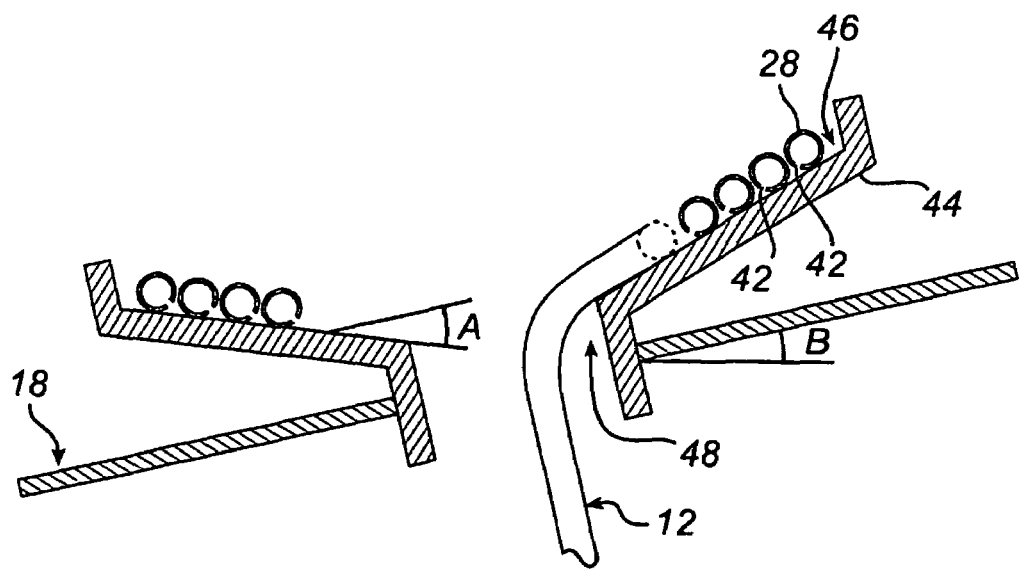
FIG. 2 is a schematic partial side view of an embodiment of the invention wherein the reference part is placed in a funnel shaped structure.
Figure 3:
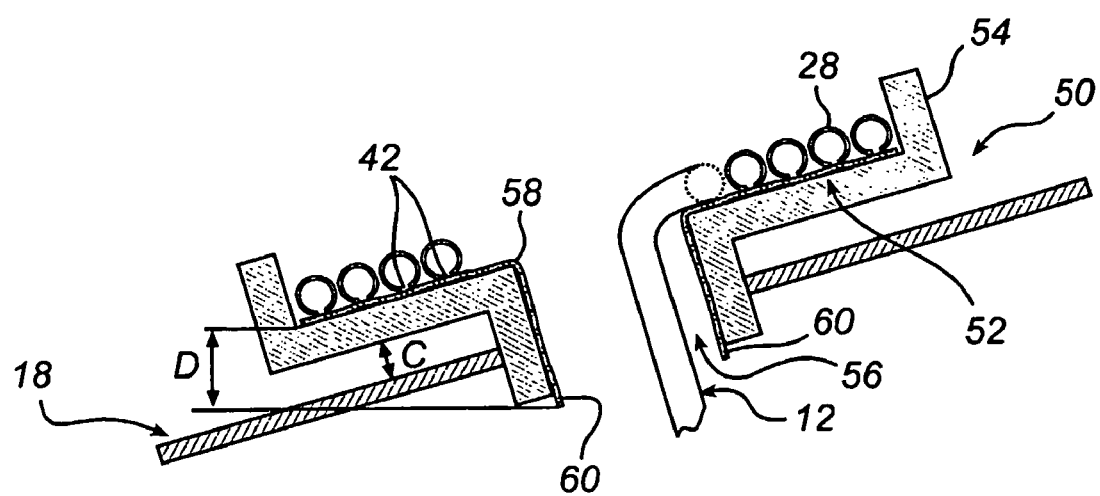
FIG. 3 is a schematic partial side view of another embodiment of the invention comprising a siphon function.

FIGS. 2-3 show embodiments of the present invention wherein the reference 28 part is situated outside of the tank. The devices in FIGS. 2-3 have the same basic structure and features as the device shown in FIG. 1, and identical reference numerals have been used for the same structures in all figures.

FIG. 2 shows a measurement device where the reference part 28 is located outside of the tank 18 in for example a boat. The reference part 28 comprises a plurality of drainage holes 42. The measurement device further comprises a funnel-like structure 44 in which the reference part 28 is arranged. The reference part 28 is shaped as an spiral, which in FIG. 2 is aligned to the inner wall 46 of the funnel 44. Alternatively, the reference part may be formed as for example a flat spiral which is positioned within the funnel 44. The bottom end opening 48 of the funnel 44 is connected to the tank 18, and the waveguide 12 enters into the tank 18 through the opening 48.

The measurement of the liquid level in the tank occurs in a manner similar to that described above regarding FIG. 1.

In the device shown in FIG. 2, excessive fluid from the fluid flow in the reference part 28 is lead out through the drainage holes 42 and returns to the tank 18 via the funnel 44. Also excessive fluid originating from for example condensation and/or fluid that enters the reference waveguide 28 from the tank 18 if the tank tilts may be led out through the drainage holes 42 and the associated funnel 44. Fluid will be led back to the tank 18 by the funnel 44 as long as the angle A of the funnel is larger than the tilt angle B of the tank. Thus, when designing the measurement device, the slope of the funnel 44 may be chosen so that the tank measurement device can manage measurements up to a predetermined maximum allowed tilt angle of the tank. In for example a boat, the maximum allowed tilt angle may be in an order of magnitude of about 25°, whereby the angle A of the funnel is set just over the chosen maximum allowed tilt angle.

Another embodiment of the invention is shown in FIG. 3. In FIG. 3, the reference part 28 of the measurement device is shaped like a flat spiral and positioned outside of the tank. The measurement device further comprises a container 50, in which the flat spiral shaped reference part is placed. The container 50 has an essentially circular base plate 52 and a wall 54 extending up from the edge of the base plate. The container 50 is connected to the tank through an opening 56 at the base plate 52, whereby the waveguide 12 passes the opening 56 in to the tank. The container 50 further comprises an absorbing layer 58 extending over the base plate 52 of the container, and down into the opening 56 to the tank. Note that the lower ends 60 of the absorbing layer 58 are positioned in the passage to the tank. The absorbing layer 58 may for example be an absorbing cloth, such as a sponge cloth.

During measurement, excess fluid, which originates from for example a flow through the reference part 28 and/or condensation, emanates from the drainage holes 42 and is absorbed by the absorbing cloth 58. Since the ends 60 of the absorbing cloth 58 are positioned at a lower level than the part of the absorbing cloth at the base plate 52 of the container 50, the fluid will accumulate in the ends 60, and drip off back into the tank 18 because of the siphon principle. Also, by elevating the container 50 off the top surface of the tank 18 a distance C, it is possible to use the siphon function, and thus the measurement device, even if the whole tank tilts, as long as the distance denoted D in FIG. 3 is larger than zero. Thus, when designing the measurement device, the elevation of the container 50 may be chosen so that the tank measurement device can manage measurements up to a desired tilt angle of the tank.

As mentioned, devices for acoustically measuring the level of a fluid in a tank, particularly a fuel tank in for example a vehicle or a boat, are known in the prior art. One such device is disclosed in UK patent application GB2 164 151, which discloses an acoustic liquid level measuring apparatus for determining the level of liquid in a tank. The apparatus comprises a tube, whereby one end of the tube is immersed in the liquid, and the other end is arranged with a transducer. The tube is also arranged with two reference means situated along the tube between the two ends of the tube. The transducer produces source pulses which are partially reflected by the reference means, and the remaining pulse energy is reflected by the liquid surface, whereby the time delays between the echoes may be used to calculate the liquid level in the tank.

When measuring with acoustic signals in a waveguide, it is advantageous to use plane wave propagation, which for example makes it possible to reduce disturbances. One condition for plane wave propagation of an acoustic signal in a waveguide is that the wavelength of the signal has to be much larger than the diameter of the waveguide. At the same time, in order to enable separation of the reflected signals, the waveguide must be several wavelengths long. Therefore, as a waveguide typically has a diameter in the order one centimeter, the waveguide in a measuring apparatus employing plane wave propagation must be very long, ranging from several decimeters up about one meter.

However, such an apparatus has the drawback that it is very elongated and requires a relatively large amount of space. When a fluid level measurement device is to be incorporated in for example a car or a truck in order to determine the fuel level in the fuel tank of the vehicle, it is of utmost importance that the measurement device does not occupy too much space. The room around the fuel tank in for example a car is usually very limited.

An object of another aspect of the present invention is therefore to provide a fluid level measurement device which is improved compared with known fluid level measurement devices.

A particular object of this further aspect of the invention is to provide a fluid level measurement device which is compact, and may be realised in a cost effective fashion.

These and other objects which will become apparent in the following description have been achieved by a device for measuring the fluid level in a tank using low frequency acoustic pulses, which device comprises a transducer for transmitting and receiving acoustic pulses, and a waveguide having one end connected to said transducer and the other end extending into the fluid, which waveguide has a reference part located above the fluid surface. The waveguide reference part is provided with at least one bend in a plane which is essentially parallel to the surface of the fluid.

This aspect of the present invention is based on the understanding that when using low frequency pulses and plane wave propagation in a waveguide, it is possible to bend and/or curve the waveguide, within certain limits, without negatively effecting the pulse propagation in the waveguide.

One advantage with the curvature of the reference part of the waveguide is that it makes it possible to realise the measurement device in a much more compact fashion. A compact size is fundamental when the fluid level measurement device is to be employed in for example a passenger car where the space around the fuel tank usually is very limited.

Another advantage when using plane wave propagation and low frequency signals is that low-cost, standard electronic components may be used in the device, which enables low manufacturing costs.

The reference part of the measurement device may be placed inside or outside of the container or tank that contains the fluid which is to be measured. Preferably, the reference part of the device is arranged in connection with the top surface of the tank. The fluid to be measured by the measurement device may be any fluid including, but not limited to gas, diesel or water.

In one embodiment, the reference part of the waveguide of the measurement device is arranged with a plurality of bends in a plane, which is essentially parallel to the surface of the fluid which is to be measured. For example, the reference part may have a reciprocating shape and extend in bends back and forth along the plane parallel to the fluid. This enables a more compact size of the measurement device.

In another embodiment, the waveguide reference part is provided in a plurality of 360°-turns in the plane essentially parallel to the fluid surface. The turns are preferably coaxial, resulting in for example a helical shape or a flat spiral shape. By helically arranging the reference part, a relatively flat reference part with a limited extension in the plane parallel to the fluid surface is achieved. Such a helical reference part may advantageously be arranged around a fuel pump in a fuel tank. In the case of a flat spiral shape, the height of the reference part is only limited by the diameter of the waveguide. This enables a very flat design of the reference part, which is a major advantage when the measurement device is to be arranged for example in connection to a fuel tank in a motorcar.

According to yet another aspect of the invention, a measurement device comprises a second waveguide having one end extending into the fluid. This makes it possible to detected the fluid level at two different positions in the tank, and thus obtain a more accurate measurement of the fluid level in a tank with irregular or restricted geometry. Such a tank may for example be a so-called saddle tank where the tank space is divided into two parts by an indentation at the bottom end of the tank. The waveguides of the measurement device may easily be extended into the more compact and restricted parts of for example such a tank, whereby the positioning of the measuring points becomes very flexible. For example, it is possible to position one measuring point in the container that usually surrounds a fuel pump, in which container the final fuel of the tank is present, and thus enabling level measurement of the very last fuel in the tank.

Note that this aspect of the invention need not be restricted to any particular form of the reference part, but is applicable to any measurement device.

The second waveguide may for example be connected to the transducer of the first waveguide. In this way, a common transducer is used. Another advantage with this arrangement is that only one opening of the tank is necessary for connecting the measurement device with electronics outside of the tank. This is advantageous since it is required by the legislation in some parts of the world that the fuel tank of a vehicle only has one opening. In this case it is possible to position the second waveguide on either the same side of the transducer as the first waveguide, or on the opposite side of the transducer, if the transducer is arranged to transmit and receive pulses in both these directions. This can facilitate attaching two waveguides to the transducer.

Alternatively, the second waveguide and the first waveguide may have a common reference part. Like above, this arrangement requires only one opening to the tank.

Another advantage is that it enables the use of a common transducer and reference part, which reduces manufacturing costs and saves space in or around the tank.

As a third alternative, the second waveguide may be connected to a second transducer. In this arrangement, the relatively more bulky parts of the measurement device, such as the transducers and the reference parts, may advantageously be placed together in a more voluminous part of the tank, while only the waveguides are extending into the more compact and restricted parts of the tank.

Figure 4:
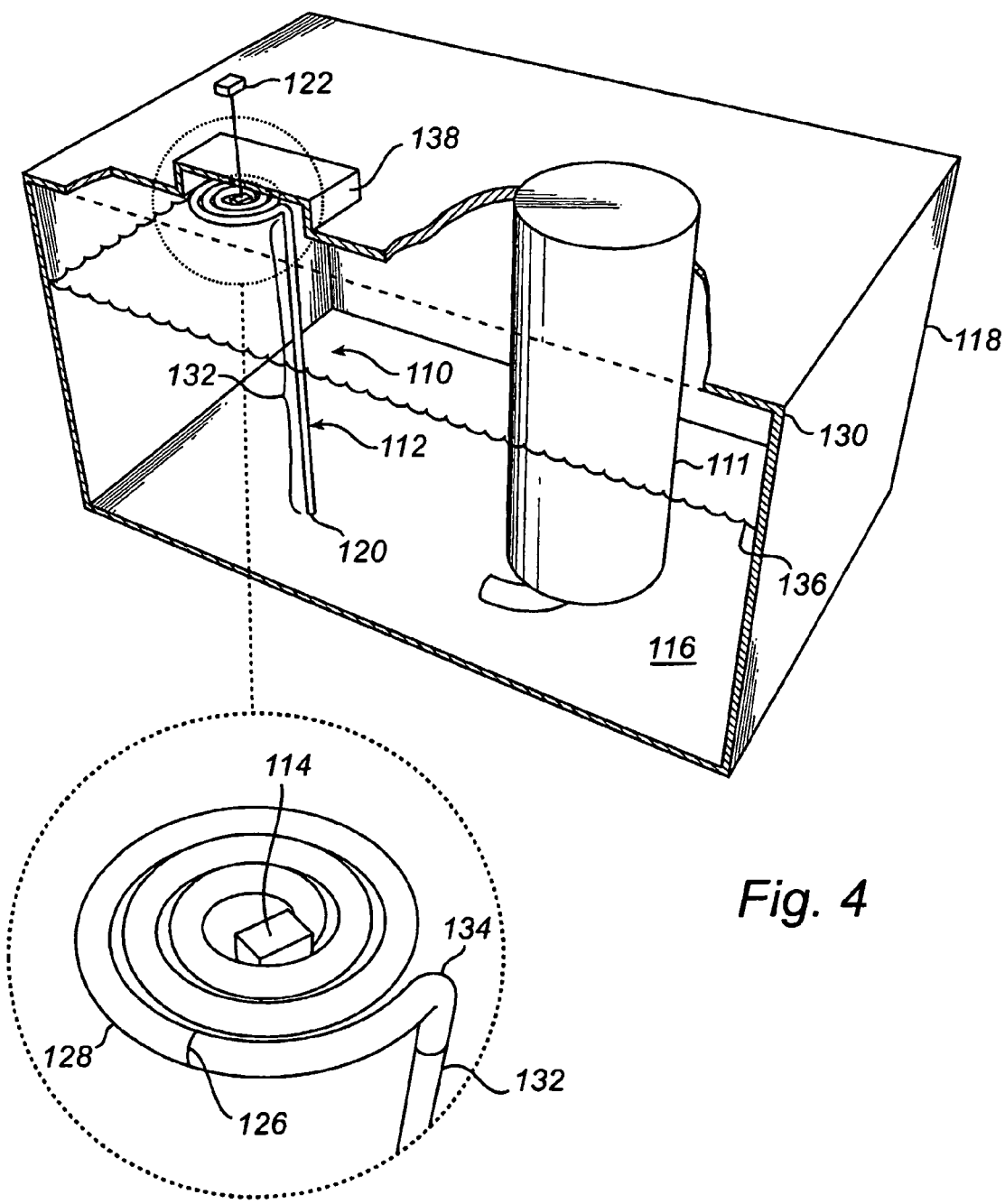
FIG. 4 is a schematic perspective view of an embodiment of the invention comprising a flat spiral shaped reference part.
Figure 5:
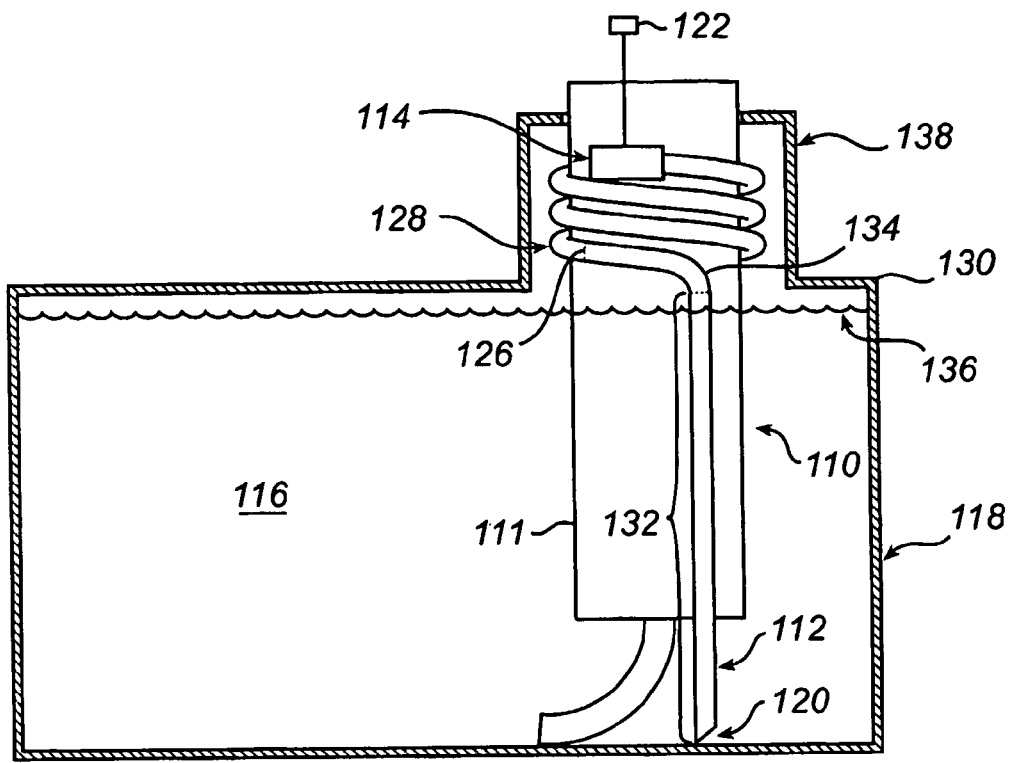
FIG. 5 is a schematic side view of an embodiment of the invention comprising a helically shaped reference part.

FIGS. 4 and 5 show a fluid level measurement device according to two embodiments of the invention. Identical reference numerals have been used for the same structures in both figures.

The measurement device is arranged to be associated with a container or tank. The tank may for example be a fuel tank of a boat or a vehicle, such as a car or a truck. The fluid which is to be measured may for example be a liquid such as petrol, diesel or water or the like. The tank shown in FIG. 4 and FIG. 5 also contains a fuel pump 11.

In FIG. 4, the measurement device 110 according to the invention comprises a waveguide 112 having one end which is connected to a transducer 114, while the other end extends into the fluid 116 which is contained in the tank 118. The end 120 of the waveguide 112 extending into the fluid 116 has an opening to allow fluid to enter the waveguide. Also, the end 120 of the waveguide extending into the fluid is preferably partially fixed to the bottom part of the tank 118. This ensures the position of the end 120 of the waveguide 112, and enables fluid level measurement from the very bottom of the tank.

The waveguide in FIG. 4 extends essentially straight down through the tank from the transducer. However, it is possible to place the measurement point, i.e. the end 120 of the waveguide, anywhere in the tank. For example the measurement point may be positioned at the centre of the bottom of the tank, even though the transducer may be positioned in for example a top corner of the tank.

The abovementioned transducer 114 may for example be a low-cost piezoelectric component, or a separate sound transmitter and sound receiver. The transducer is arranged in connection with an electronic control device 122, which is arranged to control the transducer and to calculate the fluid level based on the signals transmitted and received by the transducer.

Further, the waveguide 112 comprises a reference element 126, for example a protrusion disposed within the waveguide. The reference element 126 may for example be annularly shaped, or comprise a pin arranged in the wall of the waveguide. The part of the waveguide 112 extending from the end connected with the transducer 114 to the reference element 126 is hereinafter referred to as the reference part 128 of the waveguide. The part of the waveguide 112 from the bottom of the tank 120 to the maximum tank height 130, i.e. the highest possible fluid level, is hereinafter referred to as the measurement part 132 of the waveguide 112. The part of the waveguide 112 between the reference and measurement part is referred to as the "dead" part 134.

Figure 6A:
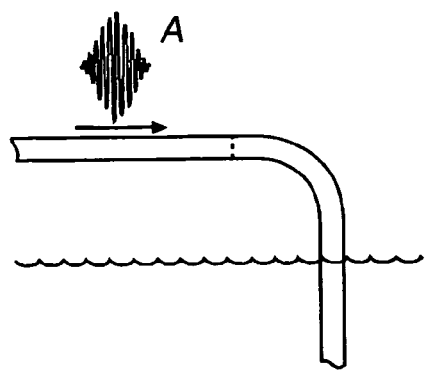
FIG. 6 is a graph showing a sequence of acoustic pulses relating to the device in FIG. 1 or FIG. 2.
Figure 6B:
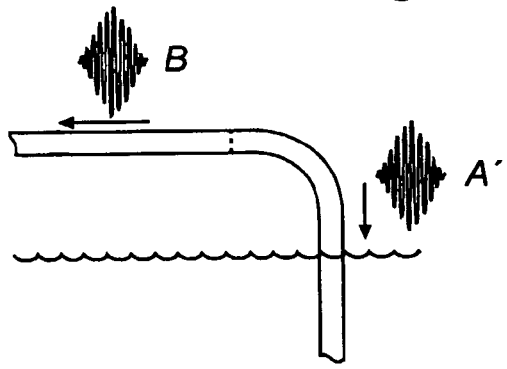

When measuring the fluid level, the transducer 114 is fed with an electric signal from the control device 122 in order to produce an sound pulse. With reference to FIG. 6a, the sound pulse A is transmitted from the transducer 114 and guided through the waveguide 112 towards the fluid surface 136. Then, as shown in FIG. 6b, the sound pulse A is partially reflected by the reference element 126, and a reflected pulse B returns toward the transducer. The remainder of the pulse A' passes the dead part 134 and travels through the measurement part 132 until it is reflected by the surface 136 of the fluid.

Figure 6C:
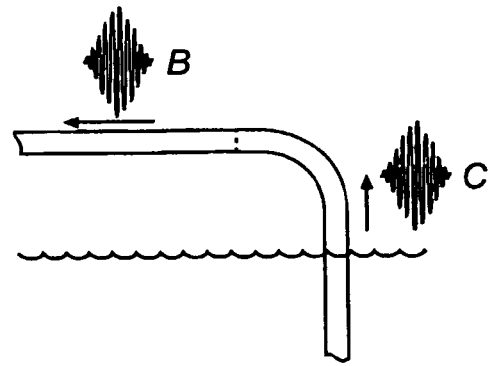

Thus, as shown in FIG. 6c, two reflected pulses B and C return to the transducer 114. One reflected pulse B is associated with the reference element, and the other reflected pulse C is associated with the surface of the fluid. As a response to the received sound pulses, the transducer 114 generates corresponding electric signals and feeds it back to the control device 122.

The dead part 134 is long enough to ensure that the two pulses B and C are sufficiently separated so that the two pulses are distinguishable, even if the tank is filled to the top and thus the pulses B and C are returning to the transducer in relatively close proximity.

By knowing the time interval between each pulse, i.e. the transit time for each acoustic pulse, and the length of the reference part 128, the dead part 134 and the measurement part 132, it is possible for the control device 122 to calculate the fluid level or fluid volume in the tank according to the following formula:

Level=(Reference part+Dead part+Measurement part)−(Reference part/REF)*SURF wherein "reference part", "dead part" and "measurement part" refers to the length of each item respectively, and REF and SURF refers to the transit time for the pulses A and B reflected by the reference element and the fluid surface respectively.

In the above formula, the fluid level is calculated by reducing the total length of the waveguide with the length of the waveguide above the surface. The length of the waveguide above the surface is calculated as the speed of sound (=Reference part/REF) times the time SURF. The speed of sound generally varies in regard of temperature and gas composition. However, since the above formula uses the speed of sound according to the reference measurement, the overall measurement is relatively insensitive regarding temperature and gas composition.

In the above embodiment, the measurement part 132 is essentially vertical and an absolute measure of the fluid level is obtained. However, it is also possible to tilt the measurement part in order to make it fit into different tanks with different heights. In that case it is advantageous to calculate the relationship between the fluid level and the maximum level of the tank in order to avoid further calibration, whereby:

Relationship=level/measurement part

According to the invention, the reference part 128 of the waveguide is curved in a plane essentially parallel to the surface 136 of the fluid. In the embodiment shown in FIG. 4, the reference part 128 is shaped like a flat spiral. This ensures that the measurement device occupies as less space as possible in connection with the tank. In FIG. 4, the reference part 128 of the waveguide is contained in a bulge 138 in the tank 118, together with the transducer 114, while the electronic control device 122 is placed outside of the tank.

Alternatively, the reference part of the waveguide may be helically shaped, as shown in FIG. 5. In FIG. 5, the reference part 128 is arranged around the fuel pump 111, and thus utilizing the space around said fuel pump. The helical reference part 128 may alternatively be placed in a similar manner to that discussed above regarding the flat spiral shaped reference, i.e. inside the tank independent of the fuel pump, for example in a bulge in the ceiling of the tank, or just outside the tank.

In the embodiments of the invention shown in FIG. 4 and FIG. 5, plane wave propagation is utilized. In order to achieve the plane wave propagation, the wavelength is much larger than the diameter of the waveguide. The wavelength should be longer than approximately the double diameter. The wavelength of the acoustic pulses is preferably in the interval about 2-10 cm, which corresponds to a frequency of about 3,4-17 kHz, i.e. not ultrasound. Because of the relatively long wavelength, the waveguide also has to be long. Preferably, the length of the reference part is up to about 70 cm, and the length of the dead part is up to about 30 cm.

Also referring to the embodiments in FIG. 4 and FIG. 5, the reference part 128 of the waveguide is contained in the tank 118, together with the transducer 114, while the electronic control device 122 is placed outside of the tank. Alternatively, the control device may be placed inside of the tank together with the transducer. However, it is also possible to place both the transducer and control device together just outside of the tank, or to place the reference part, and thus the transducer and control device, all together just outside the tank.

The waveguide 112 in FIGS. 4 and 5 may also comprise additional reference elements positioned at known distances from the first reference element 126. When using for example one additional reference element, one further sound pulse returns to the transceiver, whereby the transit time of the pulse is used to calculate the current speed of sound. Additional reference elements may for example be positioned in the measurement part, or between the transducer and the first reference element. The former results in that the reference part is closer to the fluid when the fluid level is low.

Figure 7:
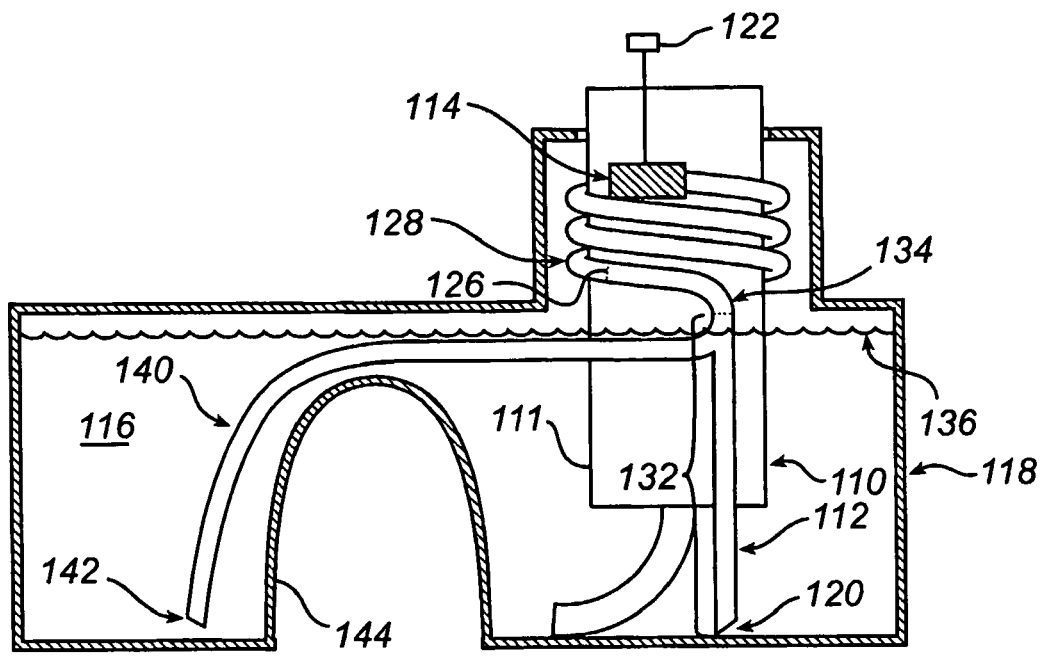
FIG. 7 is a schematic side view of an embodiment of the invention having a second waveguide and a common reference part.
Figure 8A:
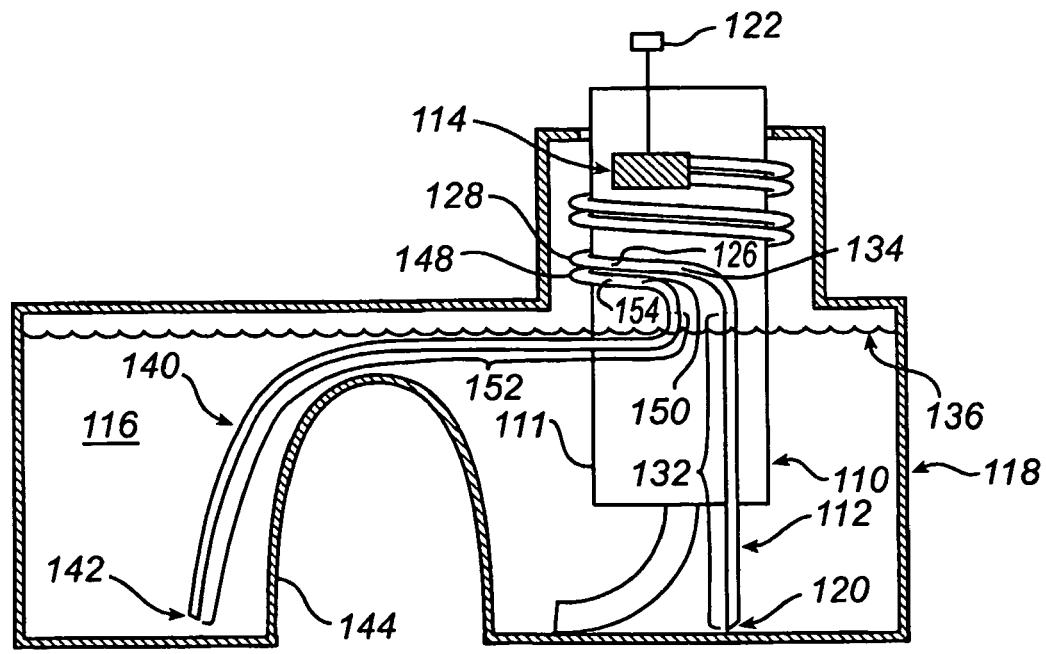
FIGS. 8a-8b is a schematic side view of an embodiment of the invention having a second waveguide and a common transducer.
Figure 8:
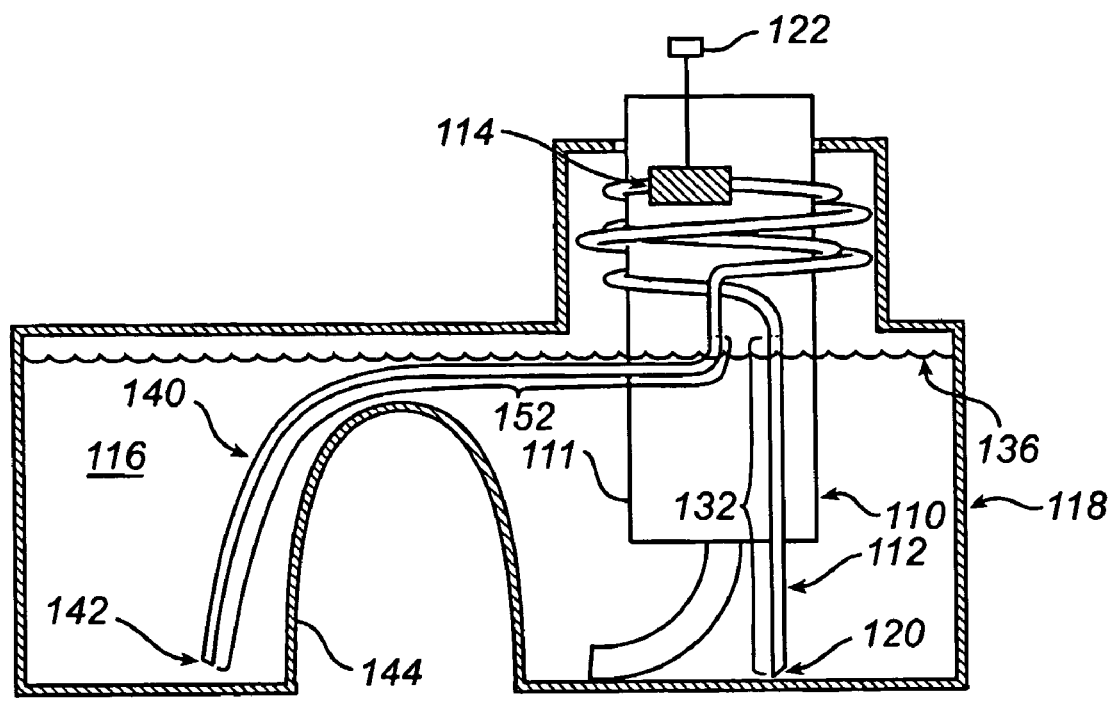
Figure 9:
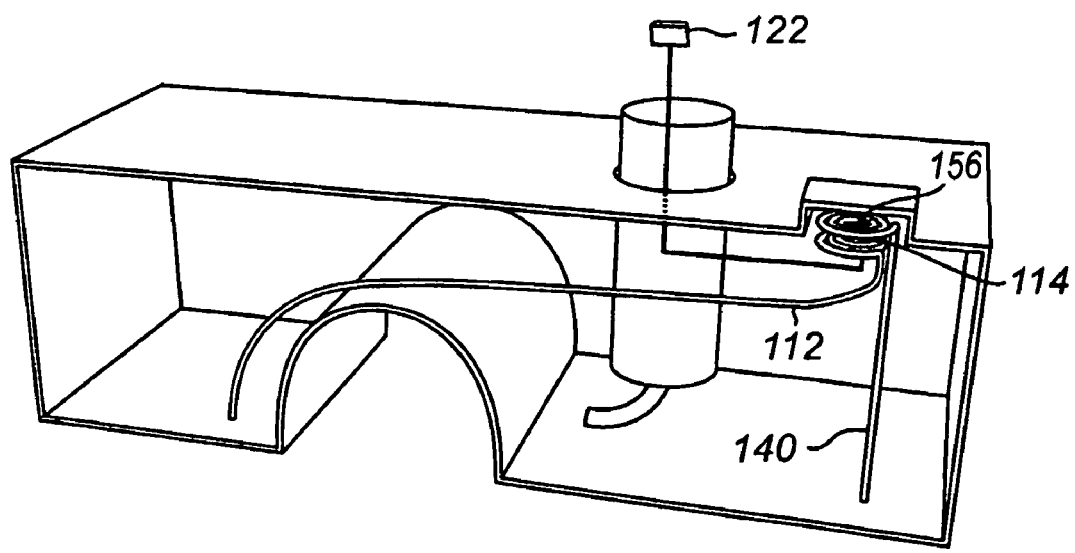
FIG. 9 is a schematic side view of an embodiment of the invention having a second waveguide and a second transducer.

FIGS. 7-9 show embodiments of the second aspect of the present invention, wherein the fluid level may be measured at two different positions in the tank. The measurement devices in FIGS. 7-9 have the same basic structure and features as the devices shown in FIGS. 4 and 5, and identical reference numerals have been used for the same structures in all figures.

FIG. 7 shows a measurement device 110 similar to that in FIG. 5, further comprising a second waveguide 140, which is connected to the end of the dead part 134 and extends into the fluid 116. The end 142 of the second waveguide extending into the fluid has an opening to allow fluid to enter the waveguide 140. Also, the end 142 is preferably placed at different position compared to the end 120 of the first waveguide 112, and partially fixed to the bottom part of the tank 118 to ensure the position of the end of the waveguide.

The tank 118 in FIG. 7 is a so-called saddle-tank, which comprises an indentation 144 at the bottom of the tank, whereby one waveguide 112, 140 is arranged on each side of the indentation 144. In this way, a more accurate measurement of the fluid level in the tank is provided. Also, the measurement device is built around only a single reference part 128 and a single transducer 114 and control device 122, which enables a more cost-efficient realisation of the device, as well as enables that only one opening of the tank 118 is required for the measurement device, even though the device features two separate measurement points.

When measuring the fluid level, a sound pulse is transmitted from the transducer 114, just like was described above. After being partially reflected by the reference element 126 and having passed the dead part 134, the pulse is split up and travels through the measurement part 132 and the second waveguide 140 respectively, and is reflected by the fluid surface 136 in each guide 132, 140. Thus, three reflected pulses return to the transducer 114. One reflected pulse is associated with the reference element 126, one is associated with the surface of the fluid at the measurement part 132, and one is associated with the surface of the fluid at the second waveguide 140. The measurement part 132 and the second waveguide 140 needs to be of different lengths so that it is possible to distinguish the two echoes from each other.

By knowing the time spent for each pulse, and the distance of the reference part, the dead part and the waveguides extending into the fluid, it is possible to calculate the fluid level or fluid volume in the tank. The calculation is made by the electronic control device 122.

As an alternative to FIG. 7, the second waveguide 140 may be connected to the transducer 114, which is shown in FIGS. 8a and 8b. In FIGS. 8a-8b, the second waveguide 140 comprises a reference part 148, a dead part 150 and measurement part 152 similar to the first waveguide 112. The second waveguide 140 may be positioned on either the same side of the transducer 114 as the first waveguide 112 (FIG. 8a), or on the opposite side of the transducer 114 (FIG. 8b). In FIG. 8b, the transducer 114 is arranged to transmit the pulses in both directions.

When measuring the fluid level in FIGS. 8a and 8b, a sound pulse is transmitted from the transducer 114 and guided through the waveguides 112, 140 towards the fluid surface 136. The sound pulse is partially reflected by the reference elements 126, 154 at the end of each reference part of the waveguides. The reference parts 128, 148 are so arranged that the echoes relating to the reference elements returning to the transducer 114 may be separated. The remainder of the pulse passes the dead parts 134, 150 and travels through the measurement part 132, 152 of the first and second waveguide respectively, and is reflected by the surface of the fluid.

Thus, four reflected pulses return to the transducer 112. One reflected pulse is associated with the reference element 126 of the first waveguide, one is associated with the reference element 154 of the second waveguide, one is associated with the surface of the fluid at the measurement part 132 of the first waveguide, and one is associated with the surface of the fluid at the measurement part 152 of the second waveguide. The measurement parts of the first and second waveguide need to be of different lengths so that it is possible to distinguish the two echoes from each other.

By knowing the time spent for each pulse, and the distance of the reference parts, the dead parts and the waveguides extending into the fluid, it is possible to calculate the fluid level or fluid volume in the tank. The calculation is made by the electronic control device.

As a third alternative, the second waveguide 140 may be connected to a second transducer 156 as shown in FIG. 9. The second waveguide 140 and the second transducer 156 have the same structure and operation as the first waveguide 112 and the first transducer 114 in FIG. 4. The measurement parts are placed at different positions in the tank to allow a more accurate reading of the fluid level. The transducers can preferably be arranged in the same region of the tank, and are connected to a single electronic control device 122, which calculates the overall fluid level based on the individual readings of the first and second transducers 114, 156 and waveguides 112, 140.

In the embodiment shown in FIGS. 7-9, the use of two measurement points also makes it possible to provide a level measurement which is independent of the tilting of the tank. For turning movements of the tank about a single axis, one waveguide is placed at each side of the tank, whereby the time difference of the reception of the echo pulses is calculated in order to provide a tilt compensated liquid level measurement.

The invention is not limited to the embodiments described above. Those skilled in the art will recognize that variations and modifications can be made without departing from the scope of the invention as claimed in the accompanying claims.

For example, the aspect of drainage holes may be combined with any measurement device where excess fluid needs to be drained out of the waveguide.

Also, additional measurement waveguides may be connected to the measurement device, which enables measurements from different parts of a tank. In this case, a common transducer and reference part may be used.

Further, the absorbing cloth may be used in combination with any structure, such as the funnel discussed above.

Although acoustic pulses have been used in the described embodiments, the inventive measurement device may also be used with other measurement modes such as standing wave measurement.

Further, the reference parts 28, 48 of the measurement devices in FIGS. 7-9 are helical and arranged around the fuel pump 11 of the tank 18. However, the reference part may alternatively be placed at a position independent of the fuel pump, either inside or outside of the tank. The reference part may also have a different shape, for example a flat spiral shape, as in FIG. 4.

Even though two waveguides have been used in for example the measurement devices in FIGS. 7-9, further waveguides may be used in order to increase the number of measurement points.

Also, the aspect of several waveguides may be combined with any conventional device.

Further, the waveguides extending into the fluid may be conically shaped so that the diameter at the bottom of end of the waveguide is larger than the diameter at the top part of the waveguide. This enables a better relief angle.

Also, the waveguides may in whole or partly have a cross sectional design that is round, rectangular or flat or the like.

The invention claimed is:

1. A device for providing a gas composition compensated acoustic measurement of the level of a liquid in a tank, comprising:
   a transducer arranged outside said liquid for transmitting and receiving acoustic signals,
   a waveguide connected to said transducer and extending into the liquid, and
   means for feeding a flow of fluid originating from said tank into the part of said waveguide which is located above the liquid level.

2. A device according to claim 1, wherein said waveguide further comprises a reference element, whereby the part of the waveguide between said transducer and said reference element is defined as a reference part, whereby said fluid is fed into said reference part.

3. A device according to claim 1, wherein the fluid flow in said waveguide is small enough for allowing an acoustic signal to travel in said waveguide.

4. A device according to claim 1, wherein said fluid which is to be fed from said tank is a liquid.

5. A device according to claim 4, wherein said device is arranged in association with a tank 5 provided with a fuel pump, whereby the flow of fluid in the waveguide is fed from said fuel pump.

6. A device according to claim 1, wherein said fluid which is to be fed from said tank is a gas.

7. A device according to claim 1, wherein said waveguide further comprises a plurality of drainage holes to allow excessive fluid to exit the waveguide.

8. A device according to claim 7, further comprising an absorbing structure arranged adjacent to said drainage holes.

9. A device according to claim 8, wherein said absorbing structure has at least one end positioned below the rest of the absorbing structure, thereby creating a siphon effect causing absorbed fluid to accumulate in said end.

10. A device according to claim 9, wherein a part of said waveguide which is located above the liquid level is positioned outside said tank, whereby said device further comprises a funnel structure having at its bottom end an opening in connection with the tank, which funnel structure is arranged so that said waveguide passes through said opening.

11. A device according to claim 10, wherein the angle of the inner wall of said funnel structure as seen from a horizontal plane is larger than a maximum tilt angle of the tank.

12. A method for providing a gas composition compensated acoustic measurement of the level of a liquid in a tank, comprising:
   transmitting an acoustic signal from a transducer located outside said liquid into a waveguide having one end extending into the liquid,
   receiving reflected acoustic signal to said transducer from said waveguide, and
   providing a flow of fluid from said tank into a part of said waveguide which is located above the liquid level.

13. A method according to claim 12, wherein said waveguide further comprises a reference element, whereby a part of the waveguide between said transducer and said reference element is defined as a reference part, whereby said fluid is fed into said reference part.

14. A method according to claim 12, wherein said fluid flow is small enough for allowing an acoustic signal to travel in said waveguide.

15. A method according to claim 12, wherein said tank is provided with a fuel pump, whereby the flow of fluid in the waveguide is fed from said fuel pump.

16. A method according to claim 12, further comprising:
   draining excessive fluid from said waveguide by means of a plurality of drainage holes arranged in said waveguide.

17. A method according to claim 16, further comprising:
   absorbing said excessive fluid by means of an absorbing structure arranged adjacent to said drainage holes.

18. A device for measuring the level of a fluid in a tank using low frequency acoustic pulses, said device comprising:
   a transducer means for transmitting and receiving acoustic pulses at a frequency of about 3.4-17 kHz;
   a waveguide connected to said transducer and extending into the fluid, said waveguide having a reference part located above the fluid surface; and
   a second waveguide extending into the fluid, wherein
   said waveguide reference part is provided with at least one bend in a plane essentially parallel to the surface of the fluid, and
   wherein said waveguide and said second waveguide are connected to said transducer on opposite sides of said transducer respectively.

19. A device for measuring the level of a fluid in a tank using low frequency acoustic pulses, said device comprising:
   a transducer means for transmitting and receiving acoustic pulses at a frequency of about 3.4-17 kHz;
   a waveguide connected to said transducer and extending into the fluid, said waveguide having a reference part located above the fluid surface; and
   a second waveguide extending into the fluid, wherein
   said waveguide reference part is provided with at least one bend in a plane essentially parallel to the surface of the fluid, and
   wherein said waveguide and said second waveguide have a common reference part.

* * * * *